(12) United States Patent
Vellenki et al.

(10) Patent No.: US 8,841,467 B2
(45) Date of Patent: Sep. 23, 2014

(54) PROCESS FOR THE PREPARATION OF (3R, 3AS, 6AR)-HEXAHYDROFURO [2, 3-B] FURAN-3-OL

(75) Inventors: Siva Rama Prasad Vellenki, Hyderabad (IN); Arabinda Sahu, Hyderabad (IN); Nitin Ashok Shimpi, Hyderabad (IN); Anil Ponnuru, Hyderabad (IN); Satish Babu Kothari, Hyderabad (IN)

(73) Assignee: Mylan Laboratories Limited, Hyderabad (IN)

( * ) Notice: Subject to any disclaimer, the term of this patent is extended or adjusted under 35 U.S.C. 154(b) by 0 days.

(21) Appl. No.: 13/989,166

(22) PCT Filed: Jul. 14, 2011

(86) PCT No.: PCT/IN2011/000470
§ 371 (c)(1),
(2), (4) Date: May 23, 2013

(87) PCT Pub. No.: WO2012/070057
PCT Pub. Date: May 31, 2012

(65) Prior Publication Data
US 2013/0244297 A1    Sep. 19, 2013

(30) Foreign Application Priority Data
Nov. 23, 2010 (IN) .......................... 3518/CHE/2010

(51) Int. Cl.
*C07D 493/04* (2006.01)
*C07D 307/20* (2006.01)

(52) U.S. Cl.
CPC ............ *C07D 493/04* (2013.01); *C07D 307/20* (2013.01)
USPC ............................ 549/435; 549/475; 549/479

(58) Field of Classification Search
USPC ........................................... 549/435, 475, 479
See application file for complete search history.

(56) References Cited

FOREIGN PATENT DOCUMENTS

| WO | WO 01 25240 | 4/2001 |
|----|----|----|
| WO | WO 2004 033462 | 4/2004 |
| WO | WO 2010 047819 | 4/2010 |

*Primary Examiner* — Bruck Kifle
(74) *Attorney, Agent, or Firm* — Ladas & Parry LLP

(57) ABSTRACT

The present invention relates to a novel process for the preparation of (3R,3aS,6aR)-hexahydrofuro[2,3-b]furan-3-ol of formula I by reacting a compound of formula VII with the compound of formula R2-OH in the presence of haloginating agent to obtain a compound of formula VI and treating a compound of formula VI with dehaloginating agent to obtain a compound of formula V by reducing a compound of formula V, followed by cylization to obtain compound of formula IV and separating the enantiomer and diastereomers from compound of formula IV to yield a compound of formula I. Compound of formula I is useful as an intermediate in the preparation of protease inhibitors, in particular broad spectrum HIV protease inhibitors, the present invention also relates to process for the preparation of Darunavir from (3R, 3aS,6aR)-hexahydrofuro[2,3-b]furan-3-ol.

9 Claims, No Drawings

PROCESS FOR THE PREPARATION OF (3R, 3AS, 6AR)-HEXAHYDROFURO [2, 3-B] FURAN-3-OL

This application claims priority to Indian patent application No 3518/CHE/2010 filed on Nov. 22, 2010 the contents of which are incorporated by reference in their entirety.

FIELD OF THE INVENTION

The present invention relates to a process for the preparation of (3R,3aS,6aR)-hexahydrofuro[2,3-b]furan-3-ol, which is useful as an intermediate in the preparation of protease inhibitors, in particular broad spectrum HIV protease inhibitors, the present invention also relates to process for the preparation of Darunavir from (3R,3aS,6aR)-hexahydrofuro[2,3-b]furan-3-ol.

BACKGROUND OF THE INVENTION

The human immunodeficiency virus ("HIV") is the causative agent of acquired immunodeficiency syndrome ("AIDS"), a disease characterized by the destruction of the immune system, particularly of CD4$^+$ T-cells, with attendant susceptibility to opportunistic infections, and its precursor AIDS-related complex ("ARC"), a syndrome characterized by symptoms such as persistent generalized lymphadenopathy, fever and weight loss.

(3R,3aS,6aR)-hexahydrofuro[2,3-b]furan-3-ol represented by the formula (I) is a useful as intermediate for synthesis of compounds for an anti-AIDS drugs.

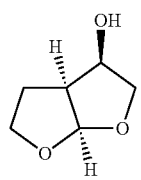

Formula-I

WO 01/25240, EP 539192-A, and Tetrahedron Letters, 1995, Vol. 36, p. 505 are discloses a process for synthesizing a racemic BIS-Tetrahydrofuran compound of formula IV using tributyltin hydride and ozone oxidation. These reagents are more hazardous and using for plant scale not suitable.

WO03024974A2 discloses the preparation of formula I is based on a photochemical cycloaddition reaction to give an oxetane intermediate which is subjected to a reduction, deprotection and rearrangement reaction. This process is cost-inefficient due to the low yields, the requisite of expensive equipment for the photochemical. This process also involves resolution in the final part of the synthesis.

US 20050256322 A1 discloses the key intermediate, an O-protected hydroxyacetyl-γ-butyrolactone, is asymmetrically hydrogenated and subsequently reduced, deprotected and cyclized to give the undesired diastereomer of compound of formula I. Further converted into desired isomer using oxidation/reduction reaction to get desired isomer. This process involve more number of steps and highly cost-inefficient.

The present invention encompassed herein an improved, commercially viable and industrially advantageous process to achieve with improved yield and purity of (3R,3aS,6aR)-hexahydrofuro[2,3-b]furan-3-ol of formula I using novel intermediates.

SUMMARY OF THE INVENTION

In one aspect of the present invention provides a process for the preparation of (3R,3aS,6aR)-hexahydrofuro[2,3-b]furan-3-ol of formula I comprising the steps of:
a) reacting a compound of formula VII with compound of formula R$_2$—OH in the presence of haloginating agent to obtain a compound of formula VI,
b) treating a compound of formula VI with dehaloginating reagent to obtain a compound of formula V,
c) reducing the compound of formula V, followed by cyclization to obtain hexahydrofuro[2,3-b]furan-3-ol of formula IV, and
d) separating the enantiomer and diastereomers from compound of formula IV to obtain a compound of formula I.

Another aspect of the present invention provides a process for the preparation of 3R,3aS,6aR)-hexahydrofuro[2,3-b]furan-3-ol of formula I comprising the steps of:
a) reacting a compound of formula VII with the compound of formula R$_2$—OH optionally in the presence of an acid to obtain a compound V,
b) reducing the compound of formula V, followed by cyclization to obtain hexahydrofuro[2,3-b]furan-3-ol of formula IV, and
c) separating the enantiomer and diastereomers from compound of formula IV to obtain a compound of formula I.

Yet another aspect of the present invention provides a process for the preparation of (3R,3aS,6aR)-hexahydrofuro[2,3-b]furan-3-ol of formula I from the recemic compound of formula IV comprising the steps of:
a) reacting hexahydrofuro[2,3-b]furan-3-ol of formula IV with an acylating agent in the presence of a base in a solvent optionally in the presence of a catalyst to obtain hexahydrofuro[2,3-b]furan-3-yl acetate of formula III,
b) hydrolyzing the hexahydrofuro[2,3-b]furan-3-yl acetate of formula III by employing an enzyme to obtain a mixture of compound of formula II and II',
c) hydrolyzing (3R,3aS,6aR)hexahydrofuro[2,3-b]furan-3-yl acetate of formula II in the presence of a base in a solvent to obtain (3R,3aS,6aR)-hexahydrofuro[2,3-b]furan-3-ol of formula I.

Yet another aspect of the present invention provides a process for preparation of substantially free diastereomers of compound of formula IV, which comprising the steps of:
a) oxidizing the mixture of enantiomers and diastereomers compound of formula IV containing the diastereomers compounds of formula IVc and IVd to obtain a keto compound of formula IV',
b) reducing the compound of formula IV' to obtain substantially free diastereomers of compound of formula IV,
wherein the mixture of enantiomer and diastereomer compound of formula IV is obtained comprising the steps of:
i) reacting a compound of formula VII with the compound of formula R2-OH in the presence of haloginating agent to obtain a compound of formula VI,
ii) treating a compound of formula VI with dehaloginating reagent to obtain a compound of formula V, and iii) reducing the compound of formula V, followed by cyclization to obtain hexahydrofuro[2,3-b]furan-3-ol of formula IV, and Yet another aspect of the present invention provides a novel intermediate of formula V

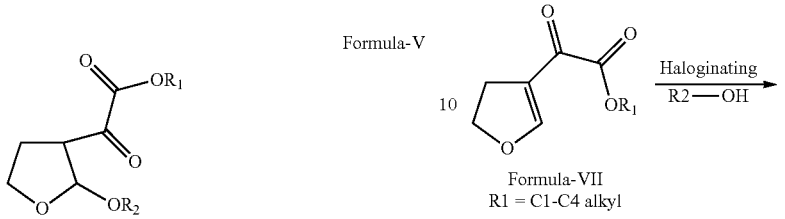

Wherein $R_1$ is $C_1$-$C_4$ alkyl and $R_2$ is $C_1$-$C_4$ alkyl or aryl.

Yet another aspect of the present invention provides a novel intermediate of formula VI.

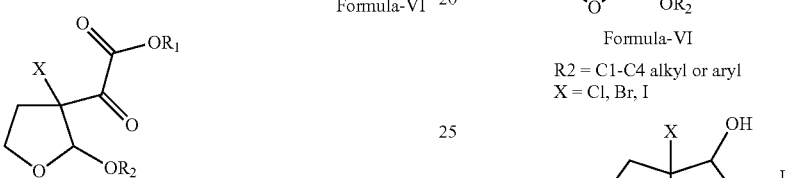

Wherein $R_1$ is $C_1$-$C_4$ alkyl, $R_2$ is $C_1$-$C_4$ alkyl or aryl and X is Cl, Br or I.

The overall synthesis of the present invention is shown in the scheme 1:

Yet another aspect of present invention is to provide a process for the preparation of compound formula I as per below scheme 2.

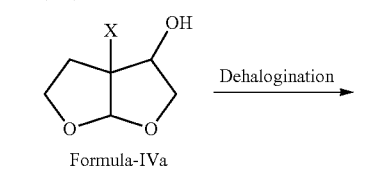

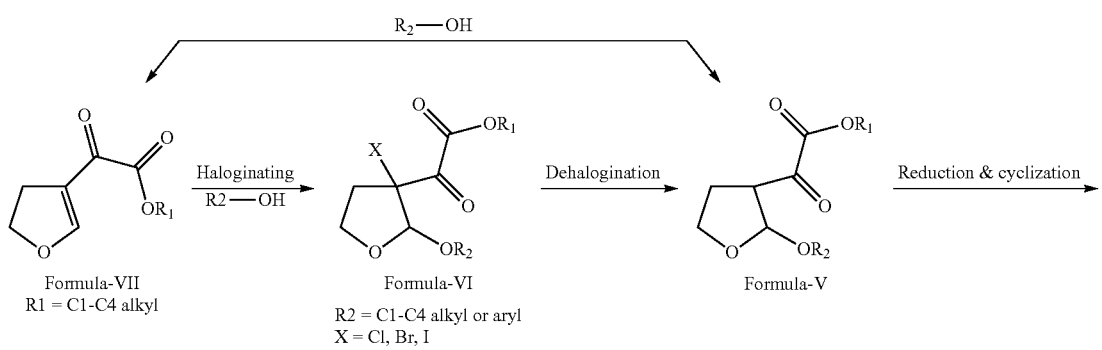

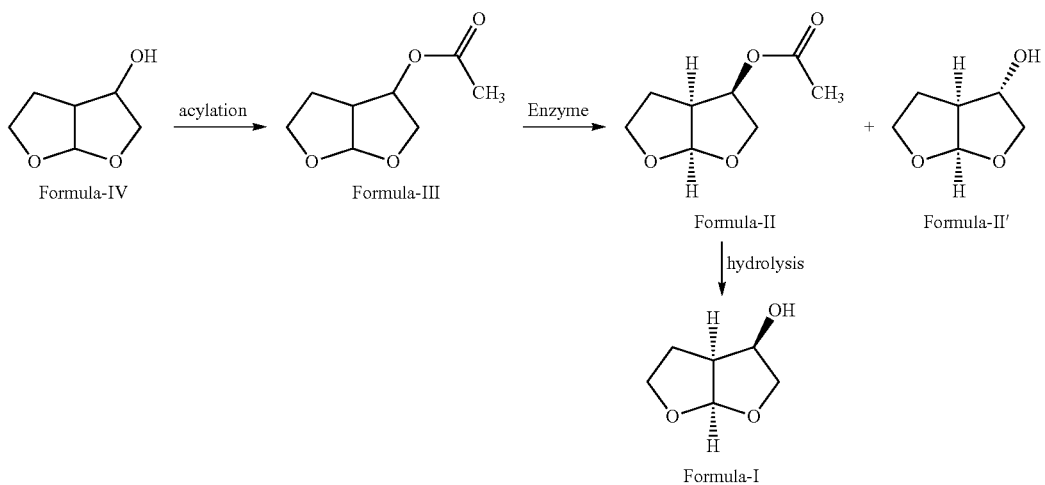

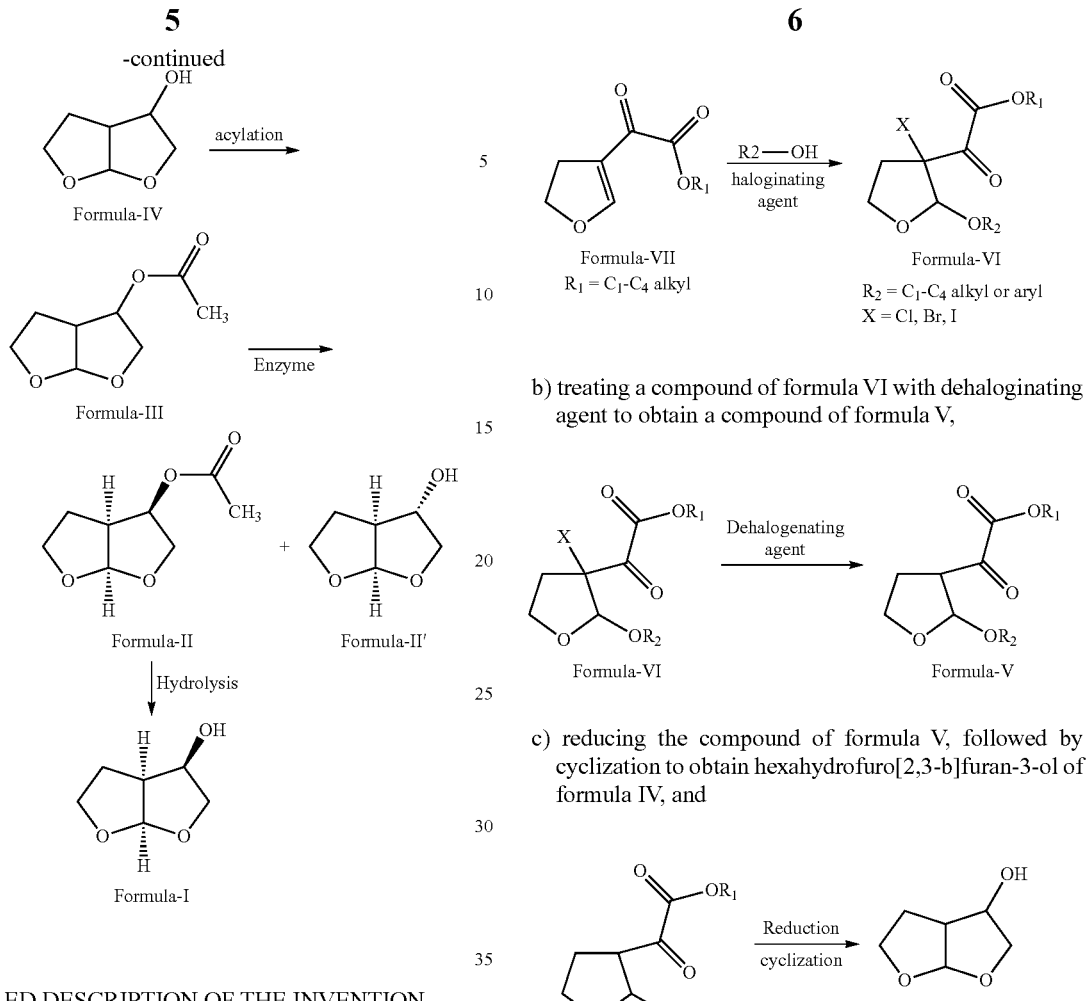

DETAILED DESCRIPTION OF THE INVENTION

The present invention relates to a novel process for the preparation of (3R,3aS,6aR)-hexahydrofuro[2,3-b]furan-3-ol of formula I by reacting a compound of formula VII with the compound of formula R2-OH in the presence of haloginating agent to obtain a compound of formula VI and treating a compound of formula VI with dehaloginating agent to obtain a compound of formula V by reducing a compound of formula V, followed by cylization to obtain compound of formula IV and separating the enantiomer and diastereomers from compound of formula IV to yield a compound of formula I.

In one embodiment of the present invention provides a process for the preparation of Hexahydrofuro[2,3-b]furan-3-ol of formula I Formula-I which comprising the steps of;
a) reacting a compound of formula VII with the compound of formula R₂—OH in the presence of haloginating agent to obtain a compound of formula VI, b) treating a compound of formula VI with dehaloginating agent to obtain a compound of formula V, c) reducing the compound of formula V, followed by cyclization to obtain hexahydrofuro[2,3-b]furan-3-ol of formula IV, and d) separating the enantiomer and diastereomers from compound of formula IV to obtain a compound of formula I.

According to present invention, compound of formula VII is reacted with formula R2-OH and halogenating agent at −15 to 15° C., preferably −5 to 10° C. to obtain compound of formula VI in a solvent selected from dichloromethane, chloroform, toluene, acetonitrile, tetrahydrofuran or mixture thereof. The halogenating agent is selected from bromine, iodine, N-bromo succinimide, N-iodo succinimide or N-chloro succinimide, preferably N-bromo succinimide.

According to present invention, compound of formula VI is treated with dehalogenating agent is selected sodium sulfite, palladium carbon with hydrogen, palladium carbon with formic acid, palladium carbon with ammonium formate, Raney Nickel with hydrogen, Raney Nickel with formic acid, Raney Nickel with ammonium formate or zinc powder.

In addition to above, the dehalogenating agents also used for this reaction selected from hydrobromic acid in the presence of a suitable halogen scavenger such as aniline or phenol or amine. The dehalogination reaction is carried out optionally in the presence of a base selected from triethylamine, pyridine or diisopropylethylamine (DIPEA). The solvent used in dehalogination reaction is selected from alcohol solvent such as ethanol, ester solvent such as ethyl acetate, chlorinated solvent such as dichloromethane, hydrocarbon solvent such as toluene, nitrile solvent such as acetonitrile, ether such as THF or mixture thereof.

According to the present invention the compound of formula V is reduced with suitable reducing agent selected from lithium borohydride, lithium aluminum hydride, diisobutylaluminium hydride, vitride, potassium borohydride or sodium borohydride, preferably sodium borohydride in a solvent selected from ethanol, methanol, toluene, tetrahydrofuran or mixture thereof at 20-70° C. and cyclization reaction is carried out using an acid selected from hydrochloric acid, hydrobromic acid, hydroiodic acid, sulfuric acid, acetic acid or sulphonic acid in a solvent selected from dichloromethane, chloroform, toluene or tetrahydrofuran at 0 to 10° C. to obtain hexahydrofuro[2,3-b]furan-3-ol of formula IV.

According to the present invention separating the recemic compound of formula IV either enzymatic separation or other methods known to a person skilled in the art for example resolution with chiral compound, that is having capable of resolving the recemic compound.

Yet another embodiment of the present invention provides a process for the preparation of Hexahydrofuro[2,3-b]furan-3-ol of formula I,

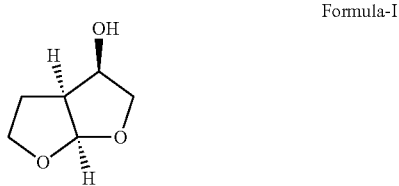

Formula-I which comprising the steps of;
a) reacting a compound of formula VII with compound of formula R$_2$—OH optionally in the presence of an acid to obtain a compound of formula V,

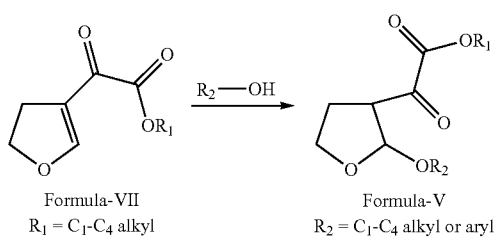

Formula-VII
R$_1$ = C$_1$-C$_4$ alkyl

Formula-V
R$_2$ = C$_1$-C$_4$ alkyl or aryl b) reducing the compound of formula V, followed by cyclization to obtain hexahydrofuro[2,3-b]furan-3-ol of formula IV, and

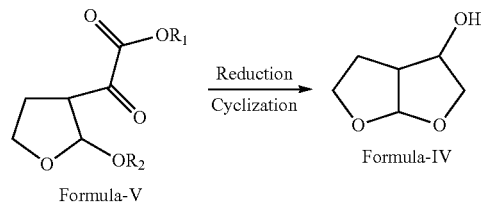

Formula-V

Formula-IV c) separating the enantiomer and diastereomers from compound of formula IV to obtain a compound of formula I.

According to present invention, compound of formula VII is reacted with formula R2-OH in a solvent selected from dichloromethane, toluene or tetrahydrofuran. Reaction is carried out optionally in the presence of an acid catalyst selected from hydrochloric acid, hydrobromic acid, methanesulfonic acid, p-toluene sulfonic acid, Lewis acid such as boron trifluoride (BF$_3$), aluminum chloride (AlCl$_3$) or titanium chloride (TiCl$_4$), at 0 to reflux temperature to obtain compound of formula V.

According to the present invention the compound of formula V is reduced with suitable reducing agent selected from lithium borohydride, lithium aluminum hydride, diisobutylaluminium hydride, vitride, potassium borohydride or sodium borohydride, preferably sodium borohydride in a solvent selected from ethanol, methanol, toluene, tetrahydrofuran or mixture thereof at 20-70° C. and cyclization reaction is carried out by using an acid selected from hydrochloric acid, hydrobromic acid, hydroiodic acid, sulfuric acid, acetic acid or sulphonic acid in a solvent selected from dichloromethane, chloroform, toluene or tetrahydrofuran at 0 to 10° C. to obtain hexahydrofuro[2,3-b]furan-3-ol of formula IV.

According to the present invention separating the recemic compound of formula IV either enzymatic resolution or other methods known to those skilled in the art for example resolution with chiral compound that is having capable of resolving the recemic compound.

According to present invention compound of formula IV having the diastereomer content in the range of 5-50%, preferably 7-20%, more preferably 7-15%.

Yet another embodiment of the present invention provides a process for the preparation (3R,3aS,6aR)-hexahydrofuro[2,3-b]furan-3-ol of formula I from recemic compound of formula IV comprising the steps of:
a) reacting hexahydrofuro[2,3-b]furan-3-ol of formula IV with acylating agent in the presence of base in a solvent to obtain hexahydrofuro[2,3-b]furan-3-yl acetate of formula III,

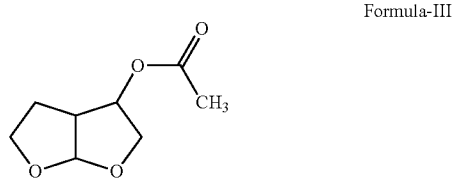

Formula-III b) hydrolyzing the hexahydrofuro[2,3-b]furan-3-yl acetate of formula III by employing an enzyme to obtain a mixture of compound of formula II and II';

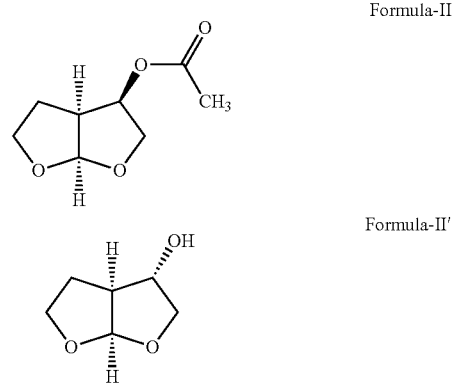

Formula-II

Formula-II' c) hydrolyzing (3R,3aS,6aR)-hexahydrofuro[2,3-b]furan-3-yl acetate of formula II in the presence of a base in a solvent to obtain (3R,3aS,6aR)-hexahydrofuro[2,3-b]furan-3-ol of formula I.

Formula-I

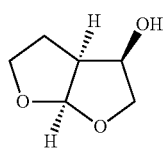

According to the present invention compound of formula IV is reacted with acylating agent selected from acetic anhydride or acetyl chloride in a solvent selected from halogenated hydrocarbon solvent such as dichloromethane, chloroform, acetonitrile, tetrahydrofuran, toluene, cyclohexane or mixture thereof in the presence of a base selected from sodium hydroxide, potassium hydroxide, sodium carbonate, potassium carbonate, diisopropyl ethyl amine, pyridine or triethyl amine at 0-30° C., optionally in presence of catalyst such as N,N-dimethylaminopyridine to get hexahydrofuro[2,3-b]furan-3-yl acetate of formula III.

According to present invention, compound of formula III is selectively hydrolyzed by treating with enzyme selected form CAL-A, CAL-B, CAL-A T2/150, CAL-B T2/150, Lipase, Lipase from *Candida rugosa*, Lipase from Hog pancreas, Lipolase-L, Amano lipase-PS, Amano lipase-AK, Amano lipase-PSD1, Amano lipase-M or Protex-6L, preferably CAL-B in buffer solution such as sodium hydrogen phosphate at 6.5 pH at 25-40° C. to obtain compound of formula II and compound of formula II'. Pure compound of formula II is obtained by separating compound of formula II' by water washings, further pure compound of formula II can be isolated by fractional distillation.

According to the present invention hydrolysis is carried out in the presence of a base is selected from metal carbonates such as sodium carbonate, metal hydroxide such as sodium hydroxide, ammonia, monomethyl amine, in a solvent selected from alcohol solvent such as methanol, halogenated solvent such as dichloromethane, ether solvent such as diisopropyl ether, hydrocarbon solvent such as toluene or mixture.

According to the present invention hexahydrofuro[2,3-b]furan-3-yl acetate of formula III and (3R,3aS,6aR)-hexahydrofuro[2,3-b]furan-3-yl acetate of formula II are purified by high vacuum fractional distillation.

According to the present invention compounds of formula II & III having the purity more than 90% by GC.

According to the present invention the compound of formula II having the enantiomeric purity not less then 99.0%, preferably 99.5% by chiral analysis.

Yet another embodiment of the present invention provides a process for preparation of substantially free diastereomers of compound of formula IV, which comprising the steps of
a) oxidizing mixture of enantiomer and diastereomer compound of formula IV containing the diastereomers compounds of formula IVc and IVd to obtain a keto compound of formula IV',

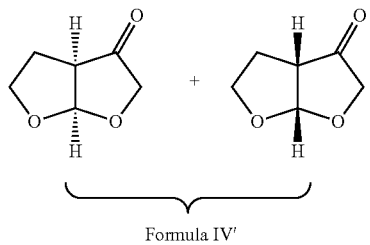 [SMILES: O=C1CO[C@H]2OCC[C@@H]12 ; O=C1CO[C@@H]2OCC[C@H]12]

Formula IV' b) reducing the keto compound of formula IV' to obtained substantially free diastereomers of compound of formula IV.

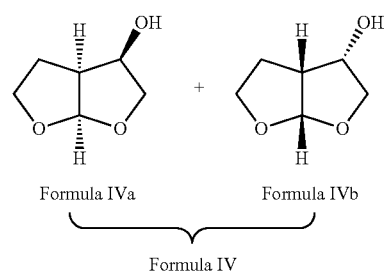 [SMILES: O[C@H]1CO[C@H]2OCC[C@H]21 ; O[C@@H]1CO[C@@H]2OCC[C@@H]21]

Formula IVa     Formula IVb

Formula IV wherein the mixture comprising a compound represented by the formula IV is obtained by a step of;
i) reacting a compound of formula VII Formula-VII

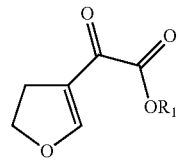

R1 = C1-C4 alkyl

With the compound of formula R2-OH in the presence of haloginating agent to obtain a compound of formula VI,

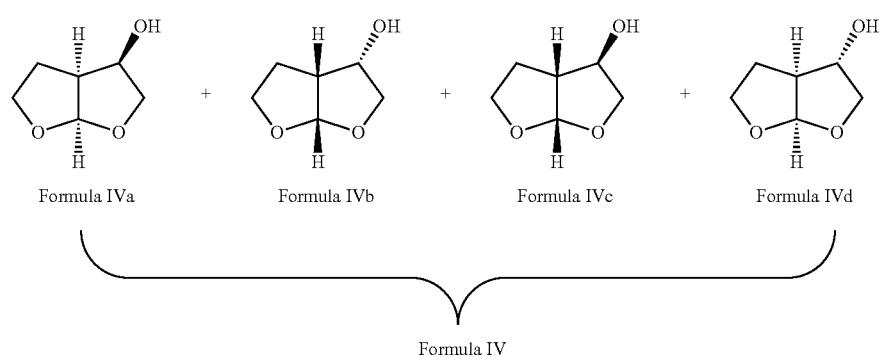

Formula IVa    Formula IVb    Formula IVc    Formula IVd

Formula IV

Formula-VI

R2 = C1-C4 alkyl or aryl
X = Cl, Br, I ii) treating a compound of formula VI with dehaloginating agent or catalyst to obtain a compound of formula V, Formula-V iii) reducing the compound of formula V, followed by cyclization to obtain hexahydrofuro[2,3-b]furan-3-ol of formula IV, Formula IV According to the present invention the oxidation reaction is carried out by oxidizing agent such as sodium hypochlorite in the presence of catalyst such as 2,2,6,6-Tetramethylpiperidin-1-yl)oxyl (TEMPO) in a solvent selected from dichloromethane, chloroform, tetrahydrofuran, methyl ter-butyl ether, di-isopropyl ether.

According to the present invention the reduction reaction of keto derivative with reducing agent such as sodium borohydride in a solvent selected from methanol, ethanol, dichloromethane or mixture thereof.

It has been observed that the above employed purification process produced substantially free diastereomers of compound of formula IV having less than about 5% of diastereomers content, preferably less than 2%.

According to the present invention isolating of keto compound of the formula IV' is in either as a solid or residue and having the purity of the compound of formula IV' of more than 95%.

Yet another embodiment of the present invention provides a novel intermediate of formula V Formula-V wherein $R_1$ is $C_1$-$C_4$ alkyl and $R_2$ is $C_1$-$C_4$ alkyl or Aryl Yet another embodiment of the present invention provides a novel intermediate of formula VI Formula-VI wherein $R_1$ is $C_1$-$C_4$ alkyl, $R_2$ is $C_1$-$C_4$ alkyl or aryl and X is Cl, Br or I Yet another embodiment of the present invention provides a process for the preparation of Darunavir (as shown in scheme-3) and other retroviral protease inhibitors using compound of formula I.

Scheme-3

Formula-1

Darunavir

According to the present invention Darunavir having the below impurity not more than 0.1, preferably 0.05%.

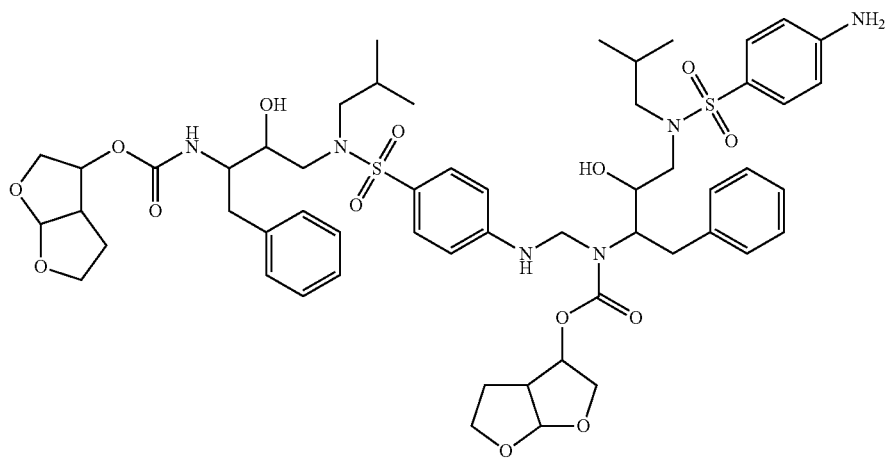 [SMILES: CC(C)CN(CC(O)C(Cc1ccccc1)NC(=O)OC1COC2OCCC12)S(=O)(=O)c1ccc(NCN(C(=O)OC2COC3OCCC23)C(Cc2ccccc2)C(O)CN(CC(C)C)S(=O)(=O)c2ccc(N)cc2)cc1]

Advantages
a) This process involves enzyme, which is eco friendly—green chemistry,
b) According to this process BIS-THF is prepared in high enantiomeric purity,
c) This process is more cost effective, commercially viable as compared to prior art process.

The examples are given solely for illustration and are not to be construed as limitations as many variations are possible without departing from spirit and scope of the invention.

EXAMPLES

Example-1

Preparation of ethyl-2-(4,5-dihydrofuran-3-yl)-2-oxoacetate 2,3-Dihydrofuran (100 gm) was taken in toluene (1000 ml) and triethyl amine (202 g) was to above solution. Ethyl oxalyl chloride (214.5 g) was slowly added to the above mixture by maintaining temp at 25-30° C. Reaction was stirred for 3 hrs. Reaction mass was washed with water (200 ml) & then with 5% sodium bicarbonate solution (2×200 ml). Reaction mass was concentrated to residue to get title compound (Yield 200 g).

1H NMR: 1.38 (t, 3H), 2.93 (t, 2H), 4.34 (q, 2H), 4.63 (t, 2H), 8.02 (s, 1H)

Example-2

Preparation of ethyl-2-(3-bromo-2-methoxytetrahydrofuran-3-yl)-2-oxoacetate

Ethyl-2-(4,5-dihydrofuran-3-yl)-2-oxoacetate (45 g) was dissolved in tetrahydrofuran (225 ml) and Methanol (45 ml). The reaction mass was cooled to −5 to 0° C. N-bromosuccinimide (47 g) was added lot wise by maintaining temp below 0° C. Reaction mass was then stirred at 20-25° C. for 12 hrs. Reaction mass was concentrated to residue under vacuum at 40° C. Residue was dissolved in Ethyl acetate (450 ml) and washed with sodium sulphite solution (10%, 2×135 ml). Reaction mass was then concentrated to residue to get ethyl-2-(3-bromo-2-methoxytetrahydrofuran-3-yl)-2-oxoacetate (Yield 63 g).

$^1$H NMR: 1.41 (t, 3H), 2.31-2.39 (m, 1H), 2.96-3.07 (m, 1H), 3.33 (s, 3H), 4.1-4.2 (m, 2H), 4.53 (q, 2H), 5.53 (s, 1H)

Example-3

Preparation of ethyl-2-(3-bromo-2-ethoxytetrahydrofuran-3-yl)-2-oxoacetate

Ethyl-2-(4,5-dihydrofuran-3-yl)-2-oxoacetate (100 g) was dissolved in dichloromethane (500 ml) and Ethanol (150 ml) was added to reaction mass and then reaction mass was cooled to 5 to 10° C. N-bromosuccinimide (115 g) was added lot wise by maintaining temp below 10° C. Reaction mass was then stirred at 20-30° C. till completion of reaction. Reaction mass was washed with sodium bicarbonate solution (8%, 3×400 ml). Reaction mass was then concentrated to residue to get Ethyl-2-(3-bromo-2-ethoxytetrahydrofuran-3-yl)-2-oxoacetate (Yield 170 g).

$^1$H NMR: 1.09 (t, 3H), 1.41 (t, 3H), 2.32-2.40 (m, 1H), 2.97-3.08 (m, 1H), 3.45-3.53 (m, 1H), 3.67-3.75 (m, 1H), 4.14-4.24 (m, 2H), 4.34 (q, 2H), 5.63 (s, 1H)

Example-4

Preparation of ethyl 2-(2-methoxytetrahydrofuran-3-yl)-2-oxoacetate

Ethyl-2-(3-bromo-2-methoxytetrahydrofuran-3-yl)-2-oxoacetate (8.5 g) was dissolved in Ethanol (85 ml). Triethyl amine (3.66 g) was added to the reaction mass. 5% Palladium on Carbon (0.85 g) was added and reaction was hydrogenated at 4-5 kg pressure of Hydrogen for 8 hrs. Reaction mass was filtered through hyflow and concentrated to residue. This residue was slurried in methyltert-butylether (42 ml) and filtered to remove triethylamine HBr salt. Filtrate was concentrated to get oily residue of Ethyl-2-(2-methoxytetrahydrofuran-3-yl)-2-oxoacetate (yield 6.0 g).

Example-5

Preparation of ethyl 2-(2-ethoxytetrahydrofuran-3-yl)-2-oxoacetate

Ethyl-2-(3-bromo-2-ethoxytetrahydrofuran-3-yl)-2-oxoacetate (100 g) dissolved in dichloromethane (500 ml). Sodium sulphite solution (15%, 1000 ml) was added to it. Reaction mass was stirred for 8 hrs. Organic and aqueous layer separated dichloromethane layer was washed with water (2×200 ml). Dichloromethane layer was then concentrated to residue to get Ethyl-2-(2-ethoxytetrahydrofuran-3-yl)-2-oxoacetate (Yield 67 g)

$^1$H NMR: 1.07 (t, 3H), 1.37 (t, 3H), 1.89-2.01 (m, 1H), 2.49-2.60 (m, 1H), 3.62-3.82 (m, 2H), 3.93-3.98 (m, 2H), 3.34-3.44 (m, 1H), 4.39 (q, 2H), 5.53 (d, 1H)

Example-6

Preparation of ethyl 2-(2-ethoxytetrahydrofuran-3-yl)-2-oxoacetate

Ethyl-2-(4,5-dihydrofuran-3-yl)-2-oxoacetate (10 g) was dissolved in Ethanol (50 ml) and Dichloromethane (50 ml). The reaction mass was stirred at 40-50° C. for 12 hrs. Reaction mass was concentrated to residue under vacuum at 40° C. Residue was dissolved in dichloromethane (50 ml) and washed with water (50 ml). Reaction mass was concentrated to residue to get ethyl-2-(2-ethoxytetrahydrofuran-3-yl)-2-oxoacetate (Yield 9.9 g).

Example-7

Preparation of ethyl 2-(2-ethoxytetrahydrofuran-3-yl)-2-oxoacetate

Ethyl-2-(4,5-dihydrofuran-3-yl)-2-oxoacetate (10 g) was dissolved in Ethanol (50 ml) and Methane sulphoic acid (0.1 ml) was added to it. The reaction mass was stirred at 40-50° C. for 12 hrs. Reaction mass was concentrated to residue under vacuum. Residue was dissolved in dichloromethane (50 ml) and washed with water (50 ml). Reaction mass was concentrated to residue to get ethyl-2-(2-ethoxytetrahydrofuran-3-yl)-2-oxoacetate (Yield 9.2 g).

Example-8

Preparation of ethyl 2-(2-ethoxytetrahydrofuran-3-yl)-2-oxoacetate (One Pot Process)

Ethyl-2-(4,5-dihydrofuran-3-yl)-2-oxoacetate (100 g) was dissolved in dichloromethane (500 ml). Ethanol (150 ml) was added to reaction mass and then reaction mass was cooled to 5 to 10° C. N-bromosuccinimide (115 g) was added lot wise by maintaining temp below 10° C. Reaction mass was then stirred at 20-30° C. till completion of reaction. Reaction mass was washed with sodium bicarbonate solution (8%, 3×400 ml). Sodium sulphite solution (15%, 1700 ml) was charged to dichloromethane layer. Reaction mass was stirred for 8 hrs at 25-35° C. Organic and aqueous layer separated. Dichloromethane layer was washed with water (2×340 ml). Dichloromethane layer was then concentrated to residue to get Ethyl-2-(2-ethoxytetrahydrofuran-3-yl)-2-oxoacetate (Yield 114 g)

Example-9

Preparation of hexahydrofuro[2,3-b]furan-3-ol

2 M Lithium borohydride solutions (24.7 ml) was added to the flask under nitrogen atmosphere. Ethyl-2-(2-methoxytetrahydrofuran-3-yl)-2-oxoacetate (5 g) was dissolved in THF (25 ml) and slowly added at 65-70° C. Reaction mass was then maintained at 65-70° C. for 10 hrs. Reaction mass was cooled to −10° C. and slowly added concentrated hydrochloric acid (16 ml) and stirred for 2 hrs at −5 to 0° C. Triethyl amine (14.6 ml) was added to the reaction mass. Reaction mass was concentrated under vacuum. Ethyl acetate (20 ml) was added and again concentrated to residue. Ethyl acetate (50 ml) was added to it and filtered the un-dissolved salts. Filtrate was concentrated to get residue of Hexahydrofuro[2,3-b]furan-3-ol (yield 1.5 g).

$^1$H NMR: 1.81-1.91 (m, 1H), 2.27-2.34 (m, 1H), 2.82-2.90 (m, 1H), 3.61-3.67 (m, 1H), 3.86-3.92 (m, 1H), 4.41-4.48 (m, 1H), 3.88-4.02 (m, 2H), 5.68 (d, 1H)

Example-10

Preparation of hexahydrofuro[2,3-b]furan-3-ol

Dissolve sodium borohydride (35.5 g) in ethanol (400 ml) under nitrogen atmosphere. Ethyl-2-(2-ethoxytetrahydrofuran-3-yl)-2-oxoacetate (100 g) was dissolved in Ethanol (100 ml) and slowly added at 15-30° C. Reaction mass was then maintained at 50-60° C. for 8 hrs. Reaction mass was cooled to 20-30° C. and slowly added ammonium chloride solution (57.5 g in 100 ml water) and stirred for 1 hrs. Reaction mass was filtered and filtrate was distilled out under vacuum to residue. Dichloromethane (400 ml) was added to residue and cooled to −10° C. Hydrochloric acid (85 ml) was added slowly drop wise in 2 hours by maintaining temp 0 to −10° C. Reaction temp was maintained for 1 hr at 0 to −10° C. Triethyl amine (91.3 g) was added to the reaction mass at 0 to −10° C. and reaction mass was stirred for 1 hour at 0 to −10° C. Reaction mass was concentrated to residue. Residue was stripped out with Ethyl acetate (2×100 ml). Ethyl acetate (500 ml) was added to the residue and cooled to 10-15° C. Reaction mass was then filtered off and filtrate was concentrated to residue to get Hexahydrofuro[2,3-b]furan-3-ol (Yield 56 g).

Example-11

Preparation of Hexahydrofuro[2,3-b]furan-3-yl acetate

Hexahydrofuro[2,3-b]furan-3-ol (25 g) was dissolved in dichloromethane (250 ml) and added triethylamine (23.3 g). N,N-dimethylaminopyridine (0.46 g) was added to the reaction mass. Reaction mass was cooled to 0-10° C. Acetic anhydride (21.5 g) was diluted with dichloromethane (50 ml) & added slowly drop-wise to the reaction mass. Reaction mass was stirred at 0-5° C. till completion. Reaction mass was washed with water (2×100 ml) & 10% Sodium chloride solution (100 ml). Reaction mass was concentrated under vacuum at <40° C. to get residue of Hexahydrofuro[2,3-b]furan-3-yl acetate (yield 29 g). Further, the product was purified by distillation (20 g) under vacuum using fractional distillation at 88-102° C. to get main fraction 17 g having purity 92.6%

$^1$H NMR: 1.9-2.09 (m, 2H), 2.10 (s, 3H), 3.0-3.1 (m, 1H), 3.86-4.03 (m, 2H), 3.73 (dd, 1H), 4.10 (dd, 1H), 5.19 (m, 1H), 5.72 (d, 1H)

Example-12

Preparation of (3R,3aS,6aR)-Hexahydrofuro[2,3-b]furan-3-yl acetate

Hexahydrofuro[2,3-b]furan-3-yl acetate (124 g) to the RB flask along with buffer solution (118 g Sodium dihydrogen phosphate dihydrate dissolved in 600 ml water & pH adjusted to 6.5 with saturated NaHCO3 aqueous solution). CAL-B enzyme (19.5 g) was added to the reaction mass and stirred at 40-45° C. Reaction was monitored by Chiral-GC. Reaction was cooled to room temp., dichloromethane (1300 ml) was charged to reaction mass and filtered through hyflow bed. Dichloromethane layer was separated and washed with Sodium chloride solution (10%, 650 ml) and water (3×650 ml). Dichloromethane layer was concentrated under vacuum to get residue of (3R,3aS,6aR)-Hexahydrofuro[2,3-b]furan-3-yl acetate (Yield 53 g). Further, the product was purified by fractional distillation under vacuum at 98-118° C. to get main fraction 39.5 g having purity 97.98%.

Example-13

Preparation of (3R,3aS,6aR)-Hexahydrofuro[2,3-b]furan-3-ol (3R,3aS,6aR)-Hexahydrofuro[2,3-b]furan-3-yl acetate (8.0 g) was dissolved in dichloromethane (24 ml) and Methanol (24 ml). Potassium carbonate (0.1 g) was added and reaction mass was stirred at 25-35° C. till the completion of reaction. Reaction mass was filtered & concentrated under vacuum at 40-45° C. to residue of (3R,3aS,6aR)-Hexahydrofuro[2,3-b]furan-3-ol (Yield 6.5 g).

Example-14

Preparation of (3R,3aS,6aR)-Hexahydrofuro[2,3-b]furan-3-ol (3R,3aS,6aR)-Hexahydrofuro[2,3-b]furan-3-yl acetate (14.0 g) was dissolved in Methanol (42 ml). Potassium carbonate (0.34 g) was added to the reaction mass. Reaction mass was stirred at 25-35° C. till the completion of reaction. Reaction mass was concentrated to residue under vacuum at 40-45° C. Dichloromethane (42 ml) was charged to residue along with activated carbon (0.7 g) and stirred for 1 hr and then filtered through hyflow bed. Filtrate was concentrated to residue to get (3R,3aS,6aR)-Hexahydrofuro[2,3-b]furan-3-ol (Yield 10.5 g)
$^1$H NMR: 1.81-1.94 (m, 1H), 2.27-2.35 (m, 1H), 2.82-2.90 (m, 1H), 3.61 (dd, 1H), 3.86-3.94 (m, 1H), 4.41 (q, 1H), 3.86-4.02 (m, 2H), 5.68 (d, 1H).

Example-15

Process for the Enhancing the Enantiomer of (3R,3aS,6aR)-Hexahydrofuro[2,3-b]furan-3-ol Hexahydrofuro[2,3-b]furan-3-ol (100 g) was dissolved in dichloromethane (700 ml) sodium bicarbonate (10%, 300 ml) was added to it and cooled to −5° C. Potassium bromide (3.7 g), 2,2,6,6-Tetramethylpiperidin-1-yl)oxyl (TEMPO) (2.4 g) and Tetrabutyl ammonium bromide (2.0 g) was added to the reaction. Sodium hypochlorite solution (670 ml) was added slowly by maintaining temp 0 to −6° C. Reaction mass was maintained at 0 to −6° C. for 1 hr. Aqueous layer was separated and extracted with dichloromethane (2×200 ml). All the dichloromethane layers were combined and washed with hydrochloride solution (10%, 200 ml) and Sodium thiosulphate solution (10%, 200 ml). Dichloromethane layer was distilled to half and then cooled to −5° C. Sodium borohydride (10.3 g) was added to the reaction mass and then methanol (100 ml) was added slowly drop-wise. Reaction mass was stirred for 2 hrs at 0 to −5° C., Acetic acid (16.1 g) was added to the reaction mass and reaction mass was distilled out residue. Methanol (200 ml) was added to it and stirred for 30 min and again concentrated to residue. Residue was strip-off with ethyl acetate (100 ml). Ethyl acetate (500 ml) was added to the residue and cooled to 10-15° C. Reaction mass was filtered. Filtrate was concentrated to get residue of Hexahydrofuro[2, 3-b]furan-3-ol (Yield 67 g).
$^1$H NMR: 1.81-1.91 (m, 1H), 2.27-2.34 (m, 1H), 2.82-2.90 (m, 1H), 3.61-3.67 (m, 1H), 3.86-3.92 (m, 1H), 4.41-4.48 (m, 1H), 3.88-4.02 (m, 2H), 5.68 (d, 1H)

Example-16

Process for the Preparation of Tetrahydrofuro[2,3-b]furan-3(2H)-one

Hexahydrofuro[2,3-b]furan-3-ol (55 g) was dissolved in dichloromethane (385 ml) sodium bicarbonate (10%, 165 ml) was added to it and cooled to −5° C. Potassium bromide (2.0 g), 2,2,6,6-Tetramethylpiperidin-1-yl)oxyl (TEMPO) (1.0 g) and Tetrabutyl ammonium bromide (1.0 g) was charged to the reaction. Sodium hypochlorite solution (365 ml) was added slowly by maintaining temp 0 to −6° C. Reaction mass was then maintained at 0 to −6° C. for 1 hr. Aqueous layer was separated and extracted with dichloromethane (2×110 ml) combined dichloromethane layers was washed with hydrochloride solution (10%, 110 ml) and Sodium thiosulphate solution (10%, 110 ml). Dichloromethane was then concentrated to residue, the residue was dissolved in isopropyl alcohol (40 ml) & methyl tert-butyl ether (40 ml) and cooled to 0-5° C., and filtered the solid to get the pure solid material of Tetrahydrofuro[2,3-b]furan-3(2H)-one (39 g) having purity 99.18%.

We claim:
1. A process for the preparation of hexahydrofuro[2,3-b]furan-3-ol of formula I,

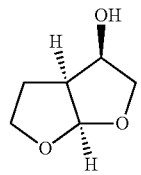

Formula-I comprising the steps of:
a. reacting a compound of formula VII with a compound of formula R2-OH in the presence of a haloginating agent to obtain a compound of formula VI;

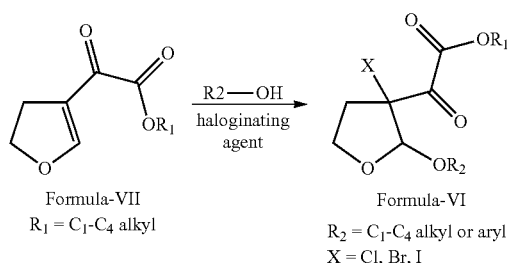

Formula-VII
$R_1 = C_1-C_4$ alkyl

Formula-VI
$R_2 = C_1-C_4$ alkyl or aryl
$X = Cl, Br, I$ b. treating the compound of formula VI with a dehaloginating agent to obtain a compound of formula V;

19

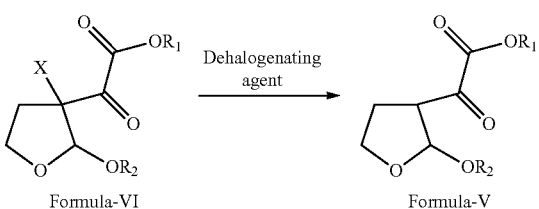

c. reducing the compound of formula V, followed by cyclization to obtain hexahydrofuro[2,3-b]furan-3-ol of formula IV; and

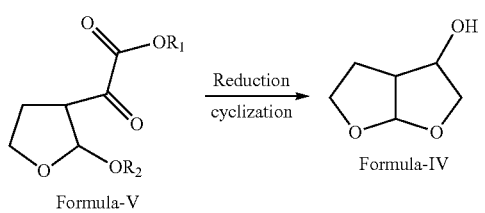

d. separating enantiomers and diastereomers of the compound of formula IV to obtain the compound of formula I.

2. A process for the preparation of hexahydrofuro[2,3-b]furan-3-ol of formula I

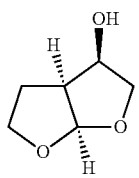

Formula-I comprising the steps of:
a. reacting a compound of formula VII with a compound of formula R₂—OH optionally in the presence of an acid to obtain a compound of formula V;

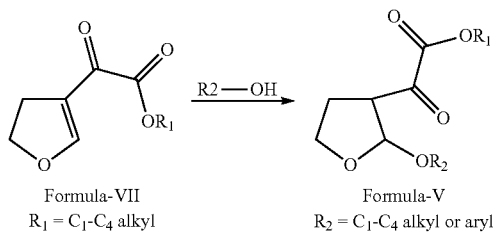

Formula-VII
R₁ = C₁-C₄ alkyl

Formula-V
R₂ = C₁-C₄ alkyl or aryl b. reducing the compound of formula V, followed by cyclization to obtain hexahydrofuro[2,3-b]furan-3-ol of formula IV; and

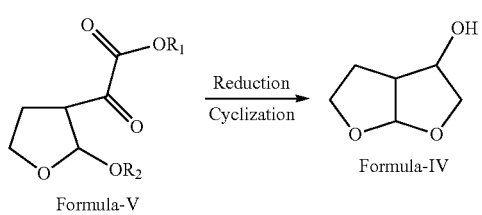

20 c. separating enantiomers and diastereomers of the compound of formula IV to obtain the compound of formula I.

3. The process according to claim 1 or 2, wherein the step of separating the enantiomers and diastereomers of the compound of formula IV to obtain the compound of formula I is carried out via an enzymatic or a chemical process.

4. A process for the preparation of (3R,3aS,6aR)-hexahydrofuro[2,3-b]furan-3-ol of formula I

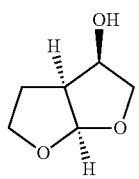

Formula-I from a compound of formula IV,

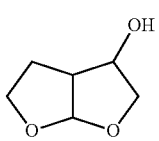

Formula-IV comprising the steps of:
a. reacting hexahydrofuro[2,3-b]furan-3-ol of formula IV with an acylating agent in the presence of a base, in a solvent, and optionally in the presence of a catalyst to obtain hexahydrofuro[2,3-b]furan-3-yl acetate of formula III;

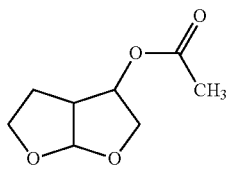

Formula-III b. hydrolyzing the hexahydrofuro[2,3-b]furan-3-yl acetate of formula III by employing an enzyme to obtain a mixture of the compounds of formula II and II'; and

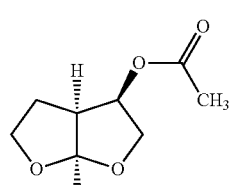

Formula-II

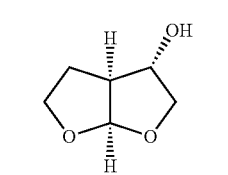

Formula-II' c. hydrolyzing the enantiomer (3R,3aS,6aR)-hexahydrofuro[2,3-b]furan-3-yl acetate of formula II in the presence of a base in a solvent to obtain (3R,3aS,6aR)-hexahydrofuro[2,3-b]furan-3-ol of formula I.

5. The process according to claim 4, wherein the catalyst used in step a) is N,N-dimethylamino pyridine.

6. A compound of formula V

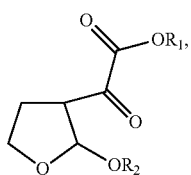

Formula-V wherein $R_1$ is $C_1$-$C_4$-alkyl and $R_2$ is $C_1$-$C_4$-alkyl or aryl.

7. A compound of formula VI

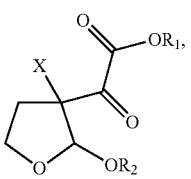

Formula-VI wherein $R_1$ is $C_1$-$C_4$-alkyl and $R_2$ is $C_1$-$C_4$-alkyl or Aryl and X is Cl, Br, or I.

8. A process for preparation of substantially free diastereomers of a compound of formula IV, comprising the steps of:
 a. oxidizing a mixture of enantiomers and diastereomers of a compound of formula IV containing the diastereomeric compounds of formula IVc and IVd

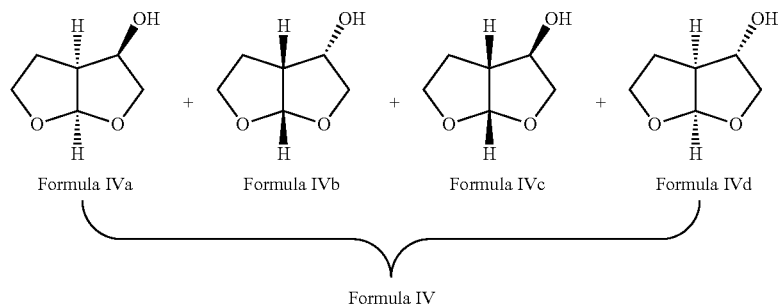 [SMILES: O[C@H]1CO[C@H]2OCC[C@H]21 ; O[C@@H]1CO[C@@H]2OCC[C@@H]21 ; O[C@H]1CO[C@@H]2OCC[C@@H]21 ; O[C@@H]1CO[C@H]2OCC[C@H]21]

Formula IV to obtain a keto compound of formula IV'; and

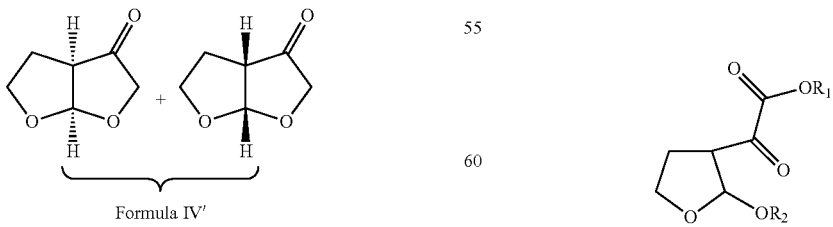

Formula IV' b. reducing the keto compound of formula IV' to obtain substantially free diastereomers of the compound of formula IV.

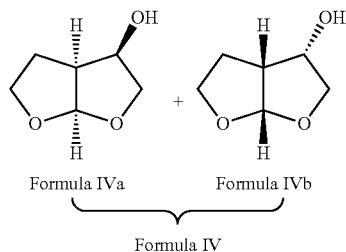

Formula IV whereby the mixture comprising the compound represented by formula IV is obtained by
 c. reacting a compound of formula VII

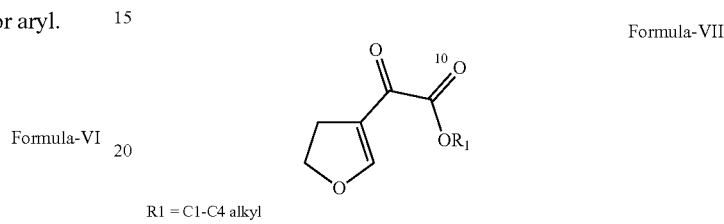

Formula-VII

R1 = C1-C4 alkyl with a compound of formula $R_2$—OH in the presence of a haloginating agent to obtain a compound of formula VI;

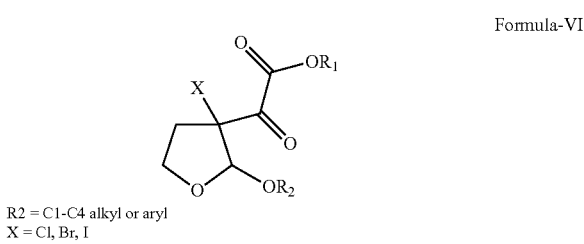

Formula-VI

R2 = C1-C4 alkyl or aryl
X = Cl, Br, I d. treating the compound of formula VI with a dehaloginating agent to obtain a compound of formula V; and

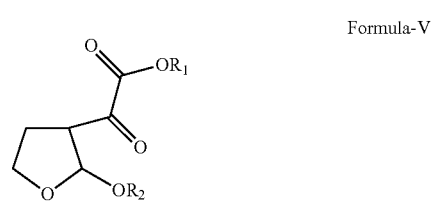

Formula-V e. reducing the compound of formula V, followed by cyclization to obtain hexahydrofuro[2,3-b]furan-3-ol of formula IV

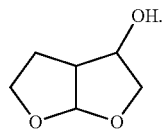
Formula-IV
9. The process according to claim 8 further comprising resolving or separating the enantiomers of the compound of formula IV to obtain the compound of formula I.
* * * * *